US00PP31867P2

(12) United States Plant Patent
Wood

(10) Patent No.: US PP31,867 P2
(45) Date of Patent: Jun. 16, 2020

(54) ***CARYOPTERIS* PLANT NAMED 'SMCIPG'**

(50) Latin Name: *Caryopteris incana*
Varietal Denomination: SMCIPG

(71) Applicant: Timothy D Wood, Spring Lake, MI (US)

(72) Inventor: Timothy D Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 0 days.

(21) Appl. No.: 16/350,976

(22) Filed: Feb. 5, 2019

(51) Int. Cl.
*A01H 5/02* (2018.01)
*A01H 6/50* (2018.01)

(52) U.S. Cl.
USPC ..... Plt./226

(58) Field of Classification Search
USPC ..... Plt./226, 263.1

CPC ... A01H 5/02; A01H 5/06; A01H 5/00; A01H 6/50

See application file for complete search history.

(56) References Cited

PUBLICATIONS

Monrovia Our 2018 New Plants Collection!, retrieved on Oct. 7, 2019, retrieved from the Internet at https://www.monrovia.com/our-2018-new-plants-collection/, 2 pp. (Year: 2019).*
Siebenthaler's Summer/Predug Wholesale Availability, retrieved on Oct. 7, 2019, retrieved from the Internet at http://siebenthaler.com/wp-content/uploads/summeravailabilitywithoutpd3s4.pdf, pp. 1 and 4. (Year: 2018).*

* cited by examiner

*Primary Examiner* — June Hwu
(74) *Attorney, Agent, or Firm* — Cassandra Bright

(57) ABSTRACT

A new and distinct *Caryopteris* cultivar named 'SMCIPG' is disclosed, characterized by attractive yellow-green foliage improved hardiness and a compact growth habit. The new variety is a *Caryopteris*, normally used for ornamental horticulture purposes.

3 Drawing Sheets

Latin name of the genus and species: *Caryopteris incana.*
Variety denomination: 'SMCIPG'.

BACKGROUND OF THE INVENTION

The new *Caryopteris* cultivar is a product of a planned breeding program conducted by the inventor, Timothy D. Wood, in Grand Haven, Mich. The objective of the breeding program was to produce improved, more cold-hardy *Caryopteris* varieties for ornamental commercial applications. The open pollination resulting in this new variety was made during August of 2005.

The seed parent is the commercial variety referred to as *Caryopteris* 'Jason'. The pollen parent is unknown as it was an open pollination breeding program. The new variety was selected July of 2013 by the inventor in a group of seedlings resulting from the 2005 open pollination, in a seedling trial field in Grand Haven, Mich.

Asexual reproduction of the new cultivar was performed by softwood cuttings. This was first performed at Spring Meadow Nursery in Grand Haven, Mich. during July of 2013 and has shown that the unique features of this cultivar are stable and reproduced true to type in 4 successive generations. First public access to plants of the variety occurred Feb. 12, 2018 in the United States. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'SMCIPG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMCIPG' These characteristics in combination distinguish 'SMCIPG' as a new and distinct *Caryopteris* cultivar:

1. Yellow-green foliage.
2. Compact growth habit.
3. Violet flowers.
4. Excellent container performance.

PARENT COMPARISON

Plants of the new cultivar 'SMCIPG' are similar to plants of the unpatented seed parent, *Caryopteris* 'Jason' in most horticultural characteristics, however, plants of the new cultivar 'SMCIPG' differ in the following;

1. New cultivar has better winter cold hardiness.
2. New variety is more compact in plant habit.

COMMERCIAL COMPARISON

Plants of the new cultivar 'SMCIPG' are comparable to the patented commercial variety *Caryopteris* 'Janice' U.S. Plant Pat. No. 22,160. The two *Caryopteris* varieties are similar in most horticultural characteristics; however, the new variety 'SMCIPG' differs in the following:

1. Comparator is more compact in habit.
2. New variety has yellow-green foliage, while the comparator has yellow foliage.
3. New variety is longer lived than this comparator.

BRIEF DESCRIPTION OF THE PHOTOGRAPHS

The accompanying photograph in FIG. 1 illustrates in full color a typical mature plant of 'SMCIPG' grown outdoors in Grand Haven, Mich. with emerging foliage in the Spring. Age of the plant photographed is approximately 2 years old from a rooted cutting.

Figure 1:
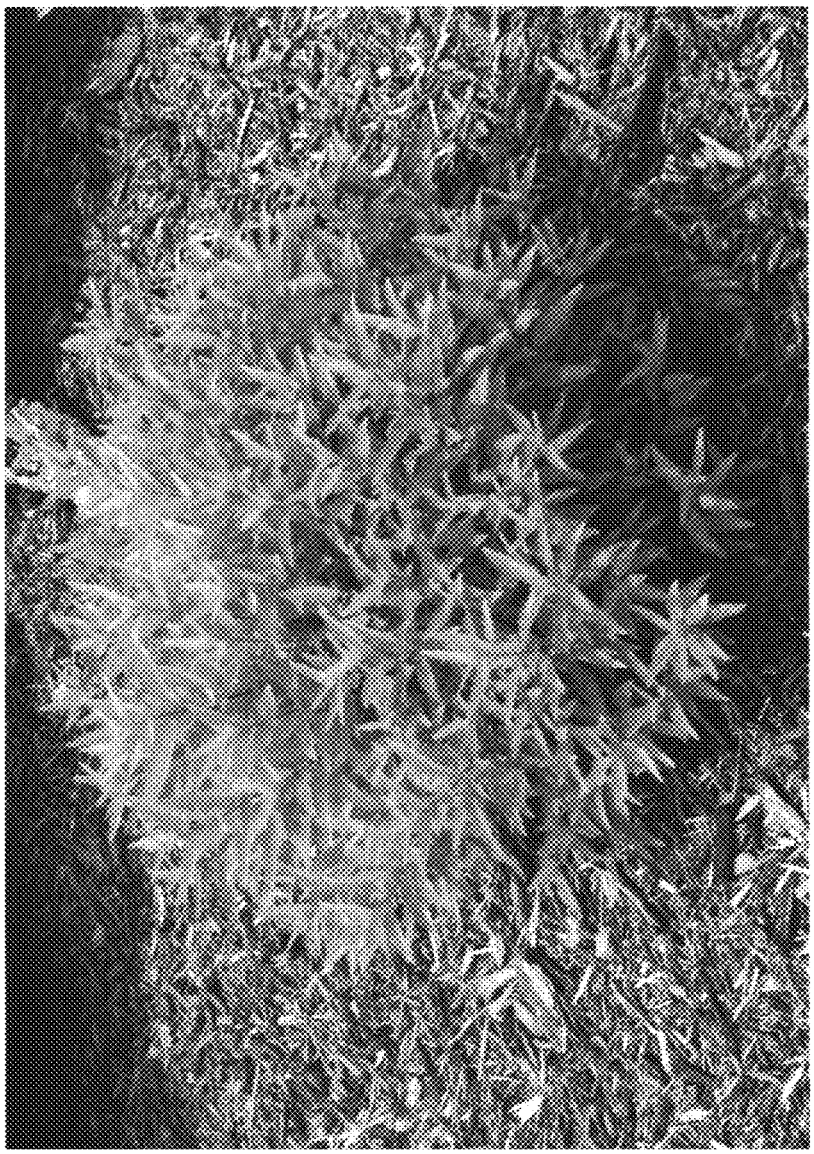
Figure 2:
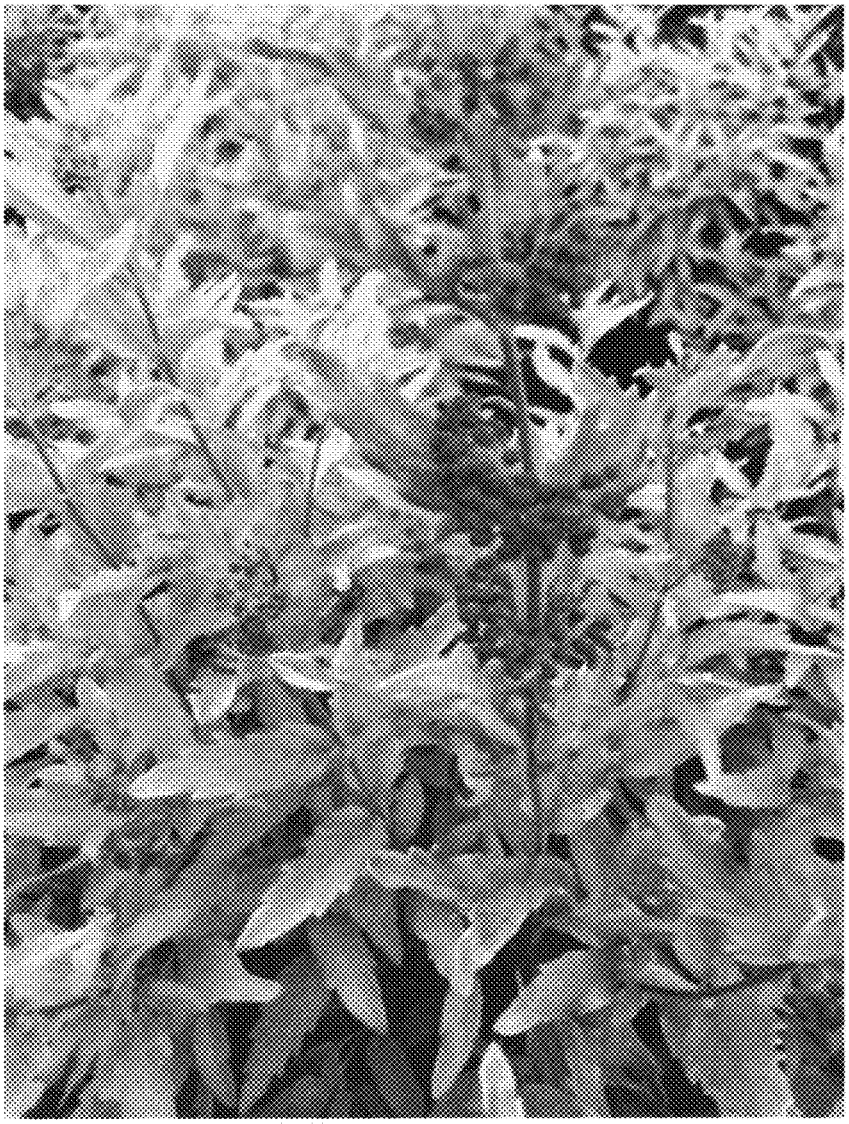
FIG. 2 illustrates a close up of the flower buds and foliage.
Figure 3:
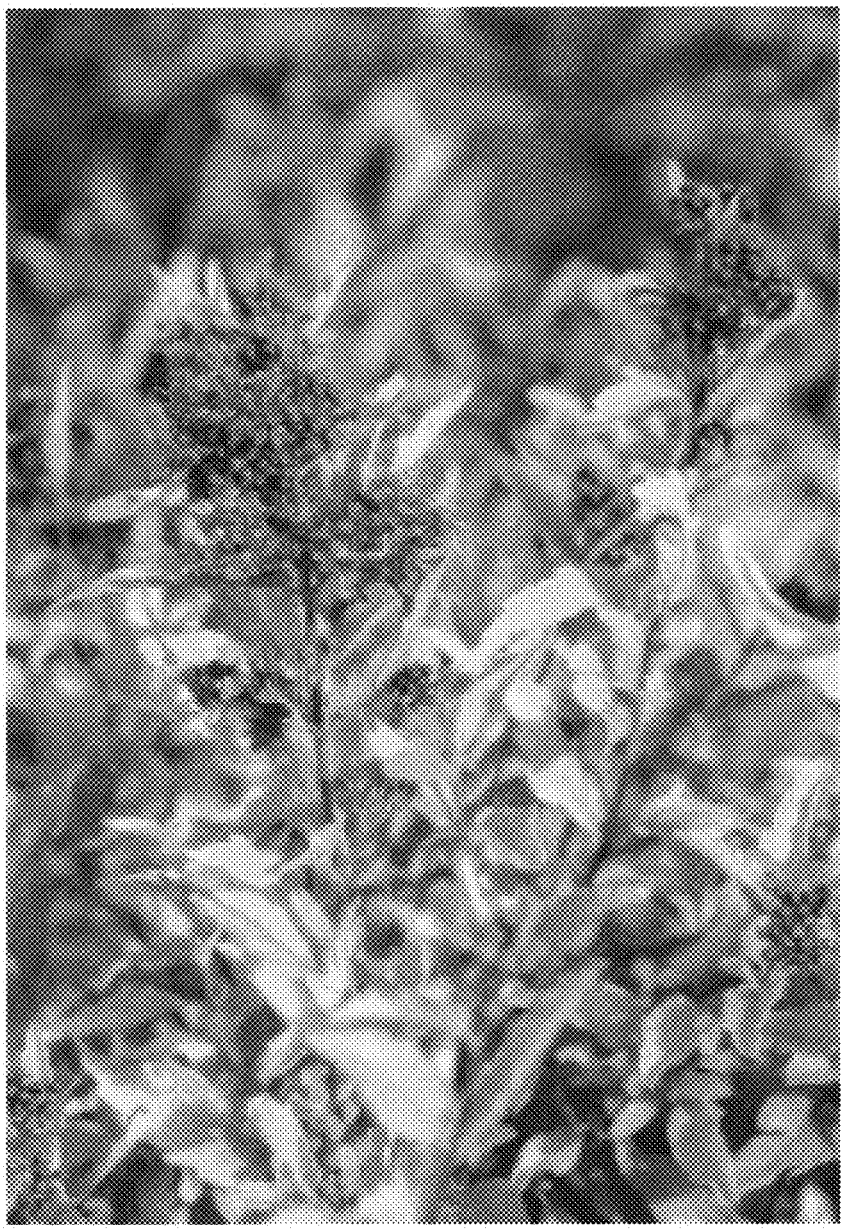
FIG. 3 illustrates a close up of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMCIPG' plants grown in a poly house during July of 2017 in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Caryopteris incana* 'SMCIPG'.

PROPAGATION

Type of propagation typically used: Softwood cuttings.

Time to initiate roots: About 7-14 days at 18-27° C.

Time to produce a rooted cutting: About 20-30 days at 18-27° C.

Root description: Fibrous, freely branching. Moderately dense, thin-medium thickness, light brown-white in color, not accurately measured with R.H.S. Chart.

PLANT

Age of plant described: 2-3 years old from rooted cutting.

Container size: 3 gallon container.

Overall plant shape: Upright, columnar, rounded.

Growth habit: Upright, outwards. Deciduous shrubby perennial.

Plant spread: 136 cm.

Plant height: 94 cm.

Growth rate: Moderate.

Plant vigor: Good.

Branching habit: Upright, outward.

Length of primary lateral branches: 69 cm.

Diameter of lateral branches: 5 mm.

Quantity of lateral branches: Approximately 12 branches.

Stem:

- *Color*.—New Growth: Near RHS Greyed-Orange 176A. Mature Growth: Near RHS Grey-Brown 199B.
- *Shape*.—Round.
- *Strength*.—Strong, somewhat flexible.
- *Angle of attachment*.—Approximately 45°.
- *Texture*.—Slightly pubescent.

Internode length: 3.25 cm.

FOLIAGE

Leaf:

- *Arrangement*.—Opposite, single.
- *Quantity*.—Average range 22 to 36 per main branch.
- *Average length*.—6 cm.
- *Average width*.—2 cm.
- *Shape of blade*.—Narrow deltoid.
- *Apex*.—Acute.
- *Base*.—Oblique.
- *Attachment*.—Stalked.
- *Margin*.—Lobed.
- *Appearance*.—Top surface shiny, bottom surface matte.
- *Texture of top surface*.—Soft.
- *Texture of bottom surface*.—Soft, ribbed.
- *Color*.—Young foliage upper side: RHS Yellow-Green 154 C. Young foliage under side: RHS Yellow-Green 151C. Mature foliage upper side: RHS Green-Yellow 1A. Mature foliage under side: RHS Yellow-Green N144B.
- *Venation*.—Type: Pinnate. Venation color upper side: Depressed, no color variation from leaf color. Venation color under side: RHS Yellow-Green 144D.
- *Petiole*.—Average Length: 1 cm. Diameter: 1 mm. Color: Upper: RHS Yellow-Green N144D. Lower: RHS Yellow-Green 144D. Texture upper and lower: Soft, velvety.

FLOWER

Natural flowering season: Spring-Summer.

Flower arrangement: Small single flowers arranged on axillary cymes.

Inflorescence form: Cyme.

Flowers and buds per plant: Thousands.

Flowers per lateral stem: About 100.

Inflorescence size:

- *Width*.—2.5 cm.
- *Height*.—2 cm.
- *Flowers and buds per inflorescence*.—About 40.

Peduncle:

- *Length*.—1.25 cm.
- *Diameter*.—1 mm.
- *Texture*.—Velvety, pubescent.
- *Color*.—RHS Yellow-green 144D.
- *Orientation*.—Upright, 15°.
- *Strength*.—Flexible.

Individual flowers:

- *Type*.—Rotate.
- *Shape*.—Zygomorphic.
- *Arrangement*.—Simple.
- *Diameter*.—Approximately 0.5 cm.
- *Length*.—7 mm.
- *Aspect*.—Upright, outward facing.
- *Persistence*.—Self-cleaning.
- *Fragrance*.—None.

Petals:

- *Arrangement*.—Whorled, petals fused.
- *Appearance*.—Small; 1-2 petals contain about 8 spurs towards the tip of the petal.
- *Number*.—5 to 6.
- *Shape*.—Obovate and spurred.
- *Margin*.—Entire.

*Tip shape*.—Emarginate and spurred.
*Base shape*.—Subulate.
*Length*.—2 mm.
*Width*.—1 mm.
*Texture*.—Upper: Smooth. Lower: Smooth.
*Color*.—When opening: Upper surface: RHS Violet-Blue 91A. Under surface: RHS Violet-Blue 91A. Fully opened: Upper surface: RHS Violet-Blue 91A. Under surface: RHS Violet-Blue 91A.

Bud:
*Shape*.—Spherical.
*Length*.—3 mm.
*Diameter*.—3 mm.
*Color*.—Near RHS Violet-Blue 91B.

Sepals:
*Appearance*.—Very small; linear.
*Arrangement*.—Whorl.
*Shape*.—Linear.
*Tip shape*.—Acute.
*Base shape*.—Fused.
*Margin*.—Entire.
*Quantity per flower*.—5.
*Length*.—1.5 mm.
*Width*.—0.5 mm.
*Margin*.—Entire.
*Texture*.—Upper: Smooth. Lower: Smooth.
*Color*.—Upper and lower: RHS Yellow-Green 144D.

Calyx:
*Shape*.—Cup.
*Length*.—2 mm.
*Diameter*.—2 mm.

Pedicel:
*Length*.—3 mm.
*Diameter*.—1 mm.
*Angle*.—0-15°.
*Strength*.—Flexible.
*Texture*.—Soft, pubescent.
*Color*.—RHS Yellow-green 144D.

REPRODUCTIVE ORGANS

Stamens:
*Number*.—4 per flower.
*Filament length*.—6 mm.
*Filament color*.—RHS Violet-Blue 94A.

Anthers:
*Shape*.—Round.
*Length*.—1 mm.
*Color*.—RHS Violet-Blue 97A.
*Pollen*.—Color: RHS Violet-Blue 97A. Quantity: Scant.

Pistil:
*Number*.—1.
*Length*.—1 cm.
*Style*.—Length: 1 cm. Color: RHS Violet-Blue 97D.
*Stigma*.—Shape: Acute. Color: RHS Violet-Blue 97D. Ovary color: RHS Yellow-Green 144B.

OTHER CHARACTERISTICS

Disease/pest resistance: Neither resistance nor susceptibility to normal diseases of *Caryopteris*. *Botrytis* is a pathogen which can be found in *Caryopteris*. Typical pests include *Prodenia*, various Aphid and mite species.

Temperature tolerance: Cold tolerant to −32° C. High temperature tolerant to 36° C.

Garden performance: Good tolerance, observed to perform well in harsh winters.

What is claimed is:

1. A new and distinct cultivar of *Caryopteris* plant named 'SMCIPG' as herein illustrated and described.

* * * * *